United States Patent [19]

Röss et al.

[11] 4,395,632

[45] Jul. 26, 1983

[54] CUVETTE FOR OPTICAL GAS-ANALYSIS APPARATUS

[75] Inventors: Rudi Röss, Bruchköbel; Helmut Heimel, Ronneburg, both of Fed. Rep. of Germany

[73] Assignee: Leybold Heraeus GmbH, Cologne, Fed. Rep. of Germany

[21] Appl. No.: 241,905

[22] Filed: Mar. 9, 1981

[30] Foreign Application Priority Data

Mar. 19, 1980 [DE] Fed. Rep. of Germany ....... 3010516

[51] Int. Cl.³ ........................................... G01N 21/26
[52] U.S. Cl. ..................................... 250/343; 250/345
[58] Field of Search ............... 250/343, 344, 345, 373; 356/246; 422/102

[56] References Cited

U.S. PATENT DOCUMENTS

| | | | |
|---|---|---|---|
| 4,175,233 | 11/1979 | DePalma et al. | 250/343 |
| 4,201,915 | 5/1980 | Schunk et al. | 250/343 |
| 4,220,415 | 9/1980 | Staab et al. | 250/343 X |
| 4,306,152 | 12/1981 | Ross et al. | 250/343 |

*Primary Examiner*—Davis L. Willis
*Attorney, Agent, or Firm*—Felfe & Lynch

[57] ABSTRACT

A cuvette for optical gas-analysis apparatus, having an elongated metallic housing with two end-faces, two chambers which are parallel to the longitudinal axis and have radiation-reflecting wall surfaces and which are separated from each other by a partition. One of the chambers is for holding a gas under investigation and the other is for holding a reference gas. The chambers are closed off at the end-faces of the housing by radiation-penetrable windows made of a material from the group consisting of calcium fluoride and barium fluoride and which are each initially connected by glass solder to an intermediate frame, which is connected to the housing. The intermediate frame has a U-shaped cross-section and is composed of a metal from the group consisting of gold, silver and aluminum and the intermediate frame is connected, to the windows and to the housing by glass solder.

2 Claims, 2 Drawing Figures

CUVETTE FOR OPTICAL GAS-ANALYSIS APPARATUS

BACKGROUND OF THE INVENTION

The invention relates to a cuvette for optical gas-analysis apparatus, particularly infra-red gas-analysis apparatus, and consisting of a metallic housing with two end-faces and a longitudinal axis and two chambers, which are parallel to the longitudinal axis and have radiation-reflecting wall surfaces and are separated from each other by a partition, one of which chambers is provided for accommodating the gas under investigation and the other for accommodating a reference gas, the chambers being closed off at the end-faces by radiation-penetrable windows made of a material from the group, calcium fluoride and barium fluoride, and which are initially connected by way of a glass solder to an intermediate frame, which is in turn connected to the housing.

DE-OS No. 27 20 636 discloses a cuvette of this kind which is arranged within a pneumatic infra-red radiation detector. This publication does not however describe in detail, the connection between the jar housing and the radiation-penetrable windows. It is simply stated that the radiation-penetrable window of the detector, which contains a micro-current sensor, is connected in a vacuum-tight manner to a thin-walled cup, made of noble metal, by means of a special glass solder.

In the manufacture of a known cuvette used in practice, the procedure has been to connect the radiation-penetrable windows to a silver intermediate frame initially by means of a glass solder. The windows prepared in this way have then been connected to the housing of the cuvette by means of a soft solder and a flux. The solder had a melting point of approximately 200° C. When soldering with a flux, there is the danger that the flux will penetrate into the zone of the radiation-reflecting wall surfaces of the cuvette and will etch them, so that the cuvettes are rendered unusable. The required radiation-reflection on the part of the wall surfaces is generally achieved by means of a very bright coating of gold. Such glass solder-metal solder connections cannot of course be used for temperatures above approximately 150° C.

It is also known to connect the radiation-penetrable windows to the housing of a cuvette by means of a synthetic resin adhesive. Although such adhesives can be used at temperatures up to approximately 250° C. and slightly more, none of these adhesives is sufficiently resistant to penetration by water-vapor. Penetration of water-vapor into the reference cell must, however, be prevented at all costs. Hitherto, special absorption means have been provided for this purpose, but their effect diminishes with rising temperatures because of increasing desorption.

SUMMARY OF THE INVENTION

The object of the present invention is therefore to improve the known cuvettes so that they become suitable for use at temperatures maintained constantly at up to 300° C. Such temperatures occur during measurements of hot gases at 250° C. for example, since, because of the radiating means present in the gas-analysis apparatus, the temperature of the cuvette can readily rise by 50° C., i.e. up to 300° C.

According to the invention, this object is achieved by means of the cuvette according to the present invention wherein the intermediate frame thereof has a U-shaped cross-section and is made of a metal from the group including gold, silver and aluminum, that the intermediate frame is connected, on the one hand, to the windows thereof and, on the other hand, to the housing by way of glass solder.

Expressed in a simple manner, the teaching of the invention covers the replacement of the connection: window-glass solder-intermediate frame-soft solder-cuvette housing by the connection- window-glass solder-intermediate frame-glass solder-cuvette housing. By dispensing with the soft solder and by means of the now exclusive use of glass solders in conjunction with the U-shaped cross-sectional form of the intermediate frame, temperature resistance of up to approximately 350° C. is achieved in long-term tests. The glass solder cannot be penetrated by water-vapor and furthermore does not cause an corrosion of radition-reflecting layers of nobel metal (gold). Any glass solder that may flow down over the noble metal does not affect the mirror coating: furthermore, because of its higher viscosity at the same temperatures, glass solder does not tend to wet the mirror coating to any great extent. Thus, spoilage during manufacture is greatly reduced.

Glass solders having a coefficient of expansion are between 110 and $150 \cdot 10^{-7}$/K have proved particularly advantagesous. Glass solders falling within the above-stated range are commercially available by quoting their coefficient of expansion. Such quotation is thus quite clear to one skilled in the art and enables the expert to obtain a suitable glass solder. A glass solder that is particularly suitable for fulfilling the stated requirements is marketed under the number 8472 by Messrs. Schott und Gen of Mainz.

The fact that a glass solder can also be used at the junction between the connecting frame and the jar housing is surprising since this housing is made of high-alloy steel or aluminum and has a considerable wall-thickness of 2 mm, and its coefficient of expansion is $160 \cdot 10^{-7}$/K or $240 \cdot 10^{-7}$/K.

The metals that might be used for the intermediate frame are gold, aluminum and preferably silver. These metals obviously bridge the various thermal expansion values of the component parts.

A form of construction of the subject matter of the invention will now be described in greater detail by reference to the following description and drawings, wherein:

DETAILED DESCRIPTION OF THE INVENTION

Figure 1:
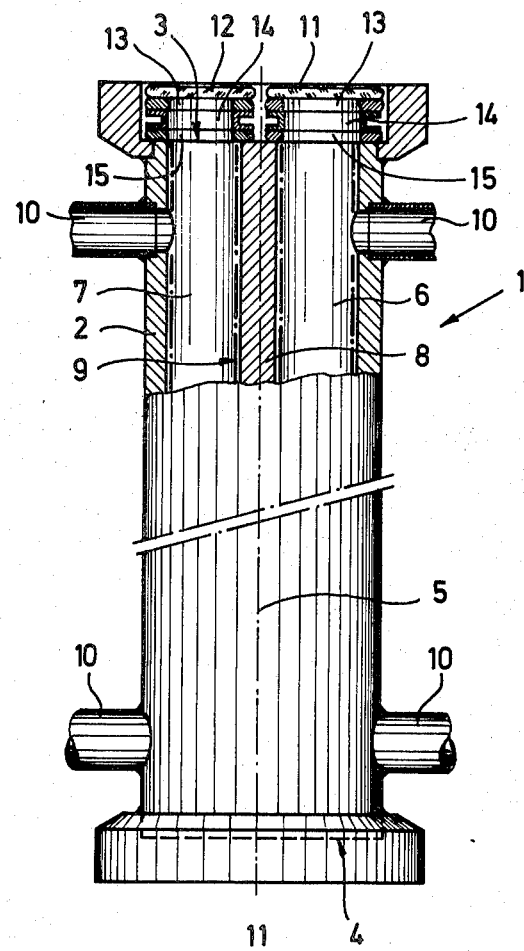
FIG. 1 is a side view of a cuvette, part of which is seen in vertical section.

FIG. 1 illustrates a cuvette 1 which consists of a metalic housing 2 having two end-faces 3 and 4. The housing has a longitudinal axis 5 and two chambers 6 and 7 which are parallel to the longitudinal axis and are formed by means of a planar diametrical partition 8. Thus the chambers 6,7 each have a cross-section in the form of a segment of a circle. One of the chambers, chamber 6, is used for accommodating and conveying a gas to be investigated whereas the other chamber 7 is provided for accommodating a reference gas for producing a reference signal. The chambers have radiation-reflecting wall surfaces, the reflecting effects being produced by means of a gold coating 9, which is illustrated in dash-dot lines. For the purpose of changing the gases, each chamber is provided with a port 10.

At the two end-faces 3 and 4, the chambers are closed off by radiation-penetrable windows 11 and 12, which are made either of calcium fluoride or barium fluoride and, in plain view, have the form of a segment of a circle which is similar to or greater than the cross-section of the chambers 6, 7. The windows 11 and 12 are each initially connected, by means of glass solder 13, to an intermediate frame 14, which has a U-shaped cross-secton and a periphery which corresponds to that of the windows 11 and 12. The intermediate frame 14 is connected in a gas-tight manner to the housing 12 by means of glass solder 15.

Figure 2:
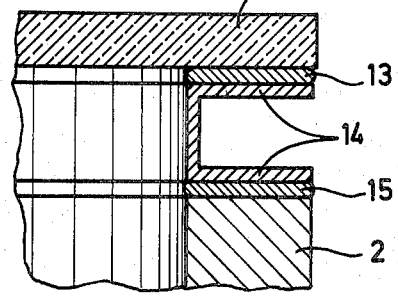
FIG. 2 shows, on a larger scale, a portion of FIG. 1.

It can be seen from FIG. 2 that a separate intermediate frame 14 is associated with each window 11 and 12, and the parallel webs of each of the two intermediate frames, disposed opposite each other in a mirror-image arrangement, are connected to the partition 8 of the housing by means of the glass solder (as seen in FIG. 1). Difficulties in forming a seal between the measuring side and the reference side are prevented by this arrangement. The arrangement illustrated at the top of FIG. 1 is also present in mirror-image form at the bottom of the apparatus of FIG. 1.

What is claimed is:

1. In a cuvette for optical gas-analysis apparatus, having an enlongated metallic housing with two end-faces, two chambers which are parallel to the longitudinal axis and have radiation-reflecting wall surfaces and which are separated from each other by a partition, wherein one of the chambers is for holding a gas under investigation and the other is for holding a reference gas, and means for closing off the chambers at the end-faces of the housing including radiation-penetrable windows made of a material from the group consisting of calcium fluoride and barium fluoride and which are each initially connected by glass solder to an intermediate frame, which is connected to the housing, the improvement wherein:
   (a) the intermediate frame has a U-shaped cross-section and is composed of a metal from the group consisting of gold, silver and aluminum, and
   (b) the intermediate frame is connected to the window and to the housing by glass solder.

2. The cuvette according to claim 1, wherein the glass solder connecting the intermediate frame to the housing and windows has a coefficient of expansion of between $110$ and $150 \cdot 10^{-7}/K$.

* * * * *